(12) United States Patent
Zeroug et al.

(10) Patent No.: US 6,941,231 B2
(45) Date of Patent: Sep. 6, 2005

(54) ACOUSTIC METHOD FOR ESTIMATING MECHANICAL PROPERTIES OF A MATERIAL AND APPARATUS THEREFOR

(75) Inventors: Smaine Zeroug, Ridgefield, CT (US); Matteo Loizzo, Rozzano (IT); Mickael Allouche, Paris (FR); Tarek Habashy, Danbury, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/451,346

(22) PCT Filed: Dec. 11, 2001

(86) PCT No.: PCT/EP01/14735
§ 371 (c)(1),
(2), (4) Date: Oct. 14, 2003

(87) PCT Pub. No.: WO02/50529
PCT Pub. Date: Jun. 27, 2002

(65) Prior Publication Data
US 2004/0054474 A1 Mar. 18, 2004

(51) Int. Cl.[7] .............................. G01B 5/28; G01B 5/30
(52) U.S. Cl. ........................................................ 702/39
(58) Field of Search .......................... 702/33, 39, 159, 702/171, 172; 73/579, 603, 624, 625

(56) References Cited
U.S. PATENT DOCUMENTS
5,741,971 A * 4/1998 Lacy ............................. 73/597

6,655,213 B1 * 12/2003 Reinhardt et al. ............ 73/597
2002/0112540 A1 * 8/2002 Zeroug et al. ................ 73/579

FOREIGN PATENT DOCUMENTS
WO        00/34769    *   6/2000

* cited by examiner

Primary Examiner—Michael Nghiem
(74) Attorney, Agent, or Firm—David Cate; Thomas O. Mitchell; Tim Curington

(57) ABSTRACT

A method and apparatus for estimating the time varying mechanical properties of a cement including propagating acoustic waves through a cement sample, measuring signals corresponding to the acoustic waves after they propagate in the sample, comparing attributes from the measured signals with corresponding attributes provided by a model accounting for at least initially estimated acoustic properties of the cement, using the differences between the measured and calculated signals to update the initially estimated acoustic properties of the material in the calculating model, using the differences between the measured and calculated signals, updating the initial acoustic properties in the model, processing N iterations of the comparison and updating either until the differences between measured and calculated signals are within a given tolerance factor or when the number i reaches a prescribed maximum and calculating the time varying mechanical properties of the cement from the final iterated acoustic properties.

25 Claims, 6 Drawing Sheets

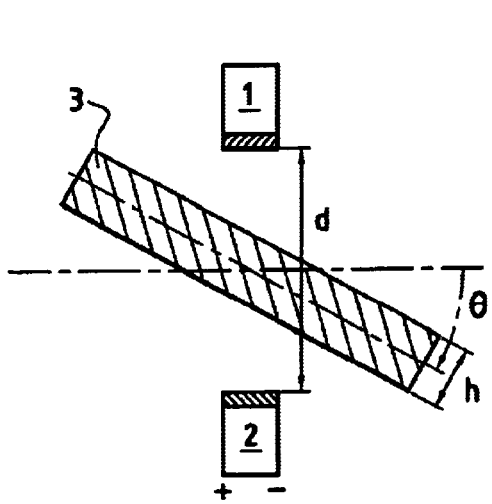
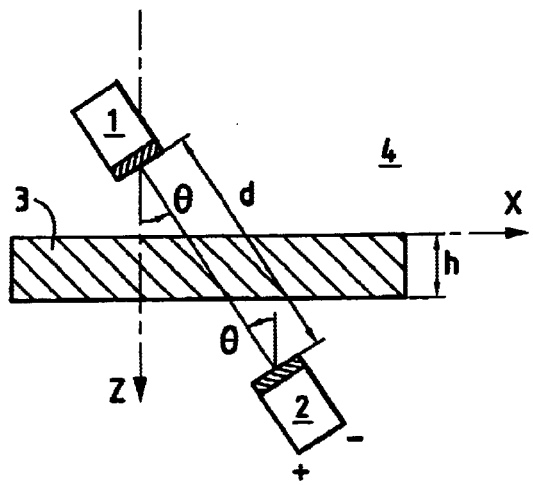
FIG.5a   FIG.5b
FIG.6
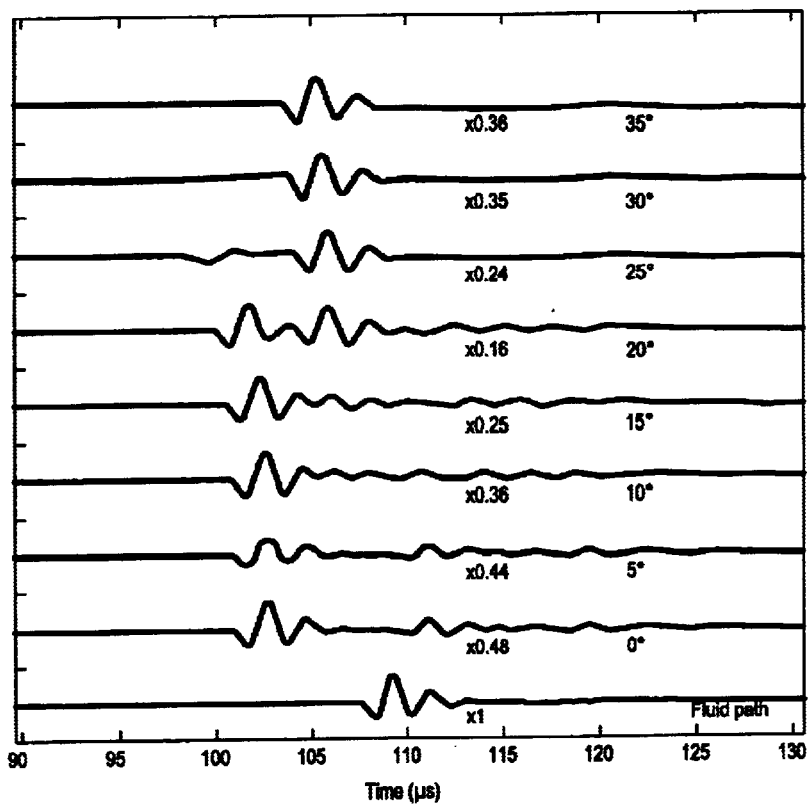

ACOUSTIC METHOD FOR ESTIMATING MECHANICAL PROPERTIES OF A MATERIAL AND APPARATUS THEREFOR

BACKGROUND OF THE INVENTION

The present invention relates to an acoustic method for estimating the mechanical properties of a material and an apparatus therefor. In particular, the invention provides a new method and apparatus for estimating the acoustic properties of set cements used in an oil well or the like.

After drilling an oil well or the like, the annular space surrounding the casing is generally cemented. Such an operation is intended to consolidate the well, to protect the casing and also, essentially, to isolate geological layers so as to prevent fluid exchange between the various formation layers, where such exchange is made possible by the path formed by the drilled hole. The cementing operation is also intended to prevent gas from rising via the annular space and to limit the ingress of water into the production well. Good isolation is thus the primary objective of the majority of cementing operations carried out in oil wells or the like.

Consequently, the selection of a cement formulation is a critical issue in such cementing operations. The appropriate cement formulation helps to achieve a durable zonal isolation, which in turn ensures a stable and productive well without requiring costly repair. Important parameters in assessing whether a cement formulation will be optimal for a particular well environment are the mechanical properties of the cement after it sets inside the annular region between casing and formation. Compressive and shear strengths constitute two important cement mechanical properties that can be related to the mechanical integrity of a cement sheath. These mechanical properties are related to the linear elastic parameters namely: Young's modulus, shear modulus, and Poisson's ratio. It is well known that these properties can be ascertained from knowledge of the cement density and the velocities of propagation of the compressional and shear acoustic waves inside said cement. Thus, ultrasonic measurements can be used: these non invasive measurements are particularly interesting as opposed to other well known mechanical techniques whereby samples are stressed to a failure stage to determine their compressive or shear strength.

Acoustic tools are usually used to perform these acoustic measurements. These tools are lowered inside a well to evaluate the cement integrity through the casing. However, interpretation of the acquired data is particularly difficult, especially due to the various compositions of the cements and data derivation induced by—among other—electronics inside said acoustic tools. Consequently, several mathematical models have already been developed to simulate the measurements, those models being very helpful to anticipate the performance of the evaluation tools as well as to interpret the tool data. However, those models necessitate the knowledge of both the velocities and attenuations of acoustic waves that propagate inside the cement. Thus, providing accurate values to those models is a very important aspect in interpreting the measurements of the different acoustic tools.

U.S. Pat. No. 4,259,868, to Rao et al, describes a device that measures compressive ultrasonic waves transit time through cement samples inserted in an auto-clave held at constant temperature and pressure. The transit time information is converted to compressive strength on the basis of established relationships between the two quantities. These relationships are obtained empirically from carrying out ultrasonic transit time measurements and mechanical compressive strength measurements on many samples. As far as the transit time of compressive ultrasonic waves decreases along the setting of the cement, the device, performed on a cement slurry, provides the cement set time, or the time it takes for the slurry to gain a minimal compressive strength, and the time for development of full compressive strength. These parameters are used as inputs for efficient scheduling and carrying out of a well cementing job. However, the reliability and accuracy of this device to provide cement compressive strength relies on the accuracy of the correlation relationships that relate compressive strength to compressional wave transit time.

An other patent U.S. Pat. No. 5,741,971 to Lacy also provides the characteristics of cement slurries measured acoustically in an auto-clave. These characteristics include dynamic Young's modulus, density, static viscosity, compressive strength and expansion or contraction of set cement. Young's modulus measurement is based on an estimation of a compressional wave transit time through a cement sample. The estimation of Young's modulus from the transit time information is based on what is believed to be an empirical relation between the two quantities. Furthermore, it is speculated that the derivation of this empirical relation is based on calibration measurements for cements with well known or independently measured Young's moduli. This patent also describes an additional empirical relation to relate the estimated Young's modulus to the unconfined compressive strength of the tested cement. This relation is derived using best fit approaches applied to data relating the two quantities where the compressive strength is measured independently using a conventional measurement.

All this embodiments of ultrasonic measurements are geared towards propagating and detecting compressional waves only. However, since shear waves only propagate through solids media, detecting shear waves in the slurry as a function of time indicates when the transition liquid to solid/gel occurs, which is an important input in determining the mechanical properties of a cement. In the U.S. Pat. No. 5,412,990, granted to D'Angelo et al, the onset of shear waves transmitted through a cement slurry is monitored and directly related to the cement thickening time. Nevertheless, as this method does not take compressional waves into account, it suffers from being inaccurate.

WO 00 34769 discloses a method for estimating the time varying properties of cement involving the propagation of acoustic signals through a sample and measuring signal corresponding thereto to determine the properties of the sample.

U.S. Pat. No. 5,001,676 describes an acoustic well logging tool that has a transducer offset from the borehole wall such that signal emitted thereby strike the borehole wall or casing at an incident angle that directs them away from the transducer.

GB 2,293,653 describes an acoustic method for non-destructive determination of porosity of a rock sample based on the travel time of shear and compressional waves from acoustic pulse between spaced transmitters and receivers.

RU 2,006,883 describes techniques for estimating the quality of cementing in a borehole using measurements of reflected acoustic waves in specified frequency ranges.

BRIEF SUMMARY OF THE INVENTION

A principle aim of the invention is to propose a method suitable for estimating the time varying mechanical properties of a material, said method being particularly accurate to provide reliable values for said time varying mechanical properties.

To this end, the invention provides a method for estimating the time varying mechanical properties of a material comprising:

propagating acoustic waves through a sample of said material;

measuring signals corresponding to said acoustic waves after they propagated in said sample. According to the invention, the method comprises:

comparing attributes from said measured signals with attributes from corresponding signals provided by a calculating model, said calculating model accounting for at least initially estimated acoustic properties of said material;

using the differences between said measured and calculated signals to update said initially estimated acoustic properties of said material in the calculating model;

processing (N) iterations of said comparisons and updatings until a given calculating stop;

calculating the time varying mechanical properties of said material from said final iterated acoustic properties.

The method according to the invention provides particularly accurate values for the time varying mechanical properties of the material because it is based on a iteration process towards the measured values, said iteration process being based upon simple and reliable parameters.

In a preferred embodiment, the acoustic waves are both compressional and shear waves, which emphasises the efficiency of the method because the correlation of the different values permits the calculated mechanical properties of the material to be checked.

According to an example of the method the measured and calculated signals are voltage values as a function of time and the attributes of the measured and calculated signals are the transit times of the acoustic waves and amplitudes of said signals. Consequently, the measured signals are very easy to acquire with conventional acoustic tools.

The acoustic properties of the material in a preferred embodiment of the method comprise the velocity of the acoustic waves through the sample of said material. These properties thus allow to easily calculate different mechanical properties of the material such as the Young's modulus, Poisson's ratio and shear modulus.

In a preferred embodiment of the method, at the $i^{th}$ iteration ($i \leq N$), the value of the velocity for the acoustic waves through the sample of material is updated according to:

$$V_l^{i+1} = V_l^i + \delta_{V_l}; \text{ where } \delta_{V_l} = -\frac{t_l^{ref} - t_l}{t_l^{ref} - (d-h)/V_f} V_l^i$$

where l means either the shear (S) or compressional (P) waves, $$t_l^{ref}$$

is the transit time of the waves in the measured signals, $t_l$ is the corresponding transit time of the calculated signal with a certain value $V_l$ for the wave velocity, d is the distance between the propagating and the measuring means, h is the sample thickness, and $V_f$ is the sound speed in the medium.

According to this preferred embodiment, the iteration stops when the relative difference between two successive iterated values of the velocity for the acoustic waves through the sample of material is within a prescribed tolerance factor $\epsilon_{V_l}$ such as:

$$\left| \frac{\delta_{V_l}}{V_l} \right| < \varepsilon_{V_l}$$

In another preferred embodiment of the method of the invention, the acoustic properties of the material comprise attenuation of the acoustic waves through the sample of material. This permits interpretation of data acquired by acoustic tools in in situ conditions, such as down an oil well.

In this preferred embodiment, at the $i^{th}$ iteration ($i \leq N$), the value of the attenuation for the acoustic wave is updated according to:

$$\alpha_l^{i+1} = \alpha_l^i + \delta_{\alpha_l}; \text{ where } \delta_{\alpha_l} = \frac{A_l^{ref} - A_l}{A_l^{ref}} \alpha_l^i$$

where l means either the shear (S) or compressional (P) waves, $$A_l^{ref}$$

is the amplitude of the acoustic waves in the measured signals and $A_l$ is the corresponding amplitude of the calculated signal with a certain value for the attenuation $\alpha_l$.

According to this embodiment, the iteration stops when the relative difference between two successive iterated values of the attenuation for the acoustic wave is within a prescribed tolerance factor $\epsilon_{\alpha_l}$ such as:

$$\left| \frac{\delta_{\alpha_v}}{\alpha_v} \right| < \varepsilon_{\alpha_l}$$

In a preferred embodiment of the method of the invention, the propagation and measuring means comprise ultrasonic compressional transducers, including a transmitter and a receiver.

The use of non-contact transducers permits avoidance of shear coupling effects typically present when using contact transducers. Actually, the shear coupling between the transducers and the sample introduces in the measured signal amplitudes non-controllable variations that can't be accounted for in the calculating method.

In another preferred embodiment of the method of the invention, the calculating model accounts for characteristics of the propagating and measuring means. These characteristics of the propagating and measuring means may comprise the radiation and the reception properties of said propagating and measuring means and the estimation of the transfer function of the electronic devices included in said means. The method according to the invention can also account for the effects of environmental parameters such as temperature and pressure.

When accounting for the different characteristics of the propagating and measuring means, the method according to the invention provides very reliable values of the mechanical characteristics of the tested material, even when environmental conditions are aggressive, for example under high temperature and/or high pressure, such as down an oil well.

It is also an aim of the invention to provide an apparatus for propagating and measuring acoustic waves through a sample of material, the mechanical properties of which vary with time, said apparatus comprising:

at least one transmitter (1) propagating said acoustic waves towards at least one receiver (2), said receiver detecting said acoustic waves after they have passed through said sample; and means for calculating properties of the sample based on the detected acoustic waves; characterised in that the apparatus comprises:

means for varying the incidence angle of the acoustic waves on the sample of the material; and means for:
comparing attributes from said detected signals with attributes from corresponding signals provided by a calculating model, said calculating model accounting for at least initially estimated acoustic properties of said material;
using the differences between said measured and calculated signals to update said initially estimated acoustic properties of said material in the calculating model;
processing (N) iterations of said comparisons and updatings until a given calculating stop;
calculating the time varying mechanical properties of said material from said final iterated acoustic properties, This apparatus can provide the measured signals that will be compared to corresponding calculated signals according to the method of the invention. The fact that the incidence angle of the acoustic waves on the sample can be varied allows both compressional and shear waves to be propagated in the sample. This permits to provide very accurate values of the mechanical characteristics of the material to be provided when combined with the method according to the invention.

BRIEF DESCRIPTION OF THE DRAWINGS

Further characteristics, advantages and details of the method and apparatus of the invention will be apparent from the description below which is made with reference to the accompanying drawings, given by way of example in which:

FIGS. 5a and 5b are the structure and geometry of the embodiment represented in FIG. 1;

FIG. 6 shows signals acquired with the embodiment of FIG. 1;

DETAILED DESCRIPTION OF THE INVENTION

As previously said, the present invention describes an acoustic method for estimating the time varying mechanical properties of a material. This method provides acoustic properties of a sample of said material, in order either to determine said time varying mechanical properties or to provide inputs in models anticipating the responses of acoustic evaluation tools, lowered for example in an oil well.

The method consists in propagating acoustic waves through a sample of material to be tested. As represented on FIGS. 1 to 5, an apparatus allows said acoustic waves, namely both compressional and shear waves, to be propagated trough a sample of material to be tested. The signals measured are then compared to corresponding signals provided by a calculating model, said calculating model accounting for acoustic properties of the material and characteristics of the propagating and measuring means. The method then uses the differences between said measured and calculated signals to update the acoustic properties of said material in the calculating model and processes N iterations of said comparison and updating either until said differences between measured and calculated signals are within a given tolerance factor or when said number N reaches a prescribed maximum. Then, the method calculates the time varying mechanical properties of said material from said final iterated acoustic properties.

Figure 1:
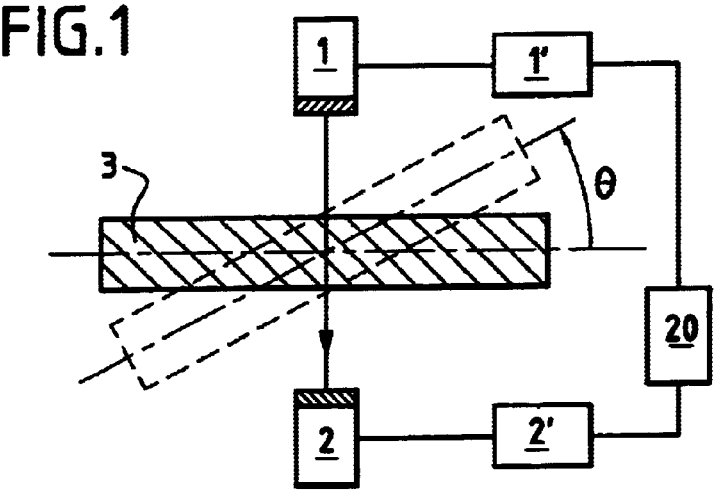
FIG. 1 is a first embodiment of the measurement apparatus of the invention.

In the first embodiment, illustrated in FIG. 1, a single ultrasonic transmitter 1 and a single ultrasonic receiver 2, both known in the state of the art (for example ultrasonically-pulsed acoustic piston transducers of about ¾ inch diameter), are facing and positioned at a distance d from each other. These transducers are surrounded by a medium 4 allowing to propagate acoustic waves, said medium being water for example. A sample of material 3, some cement for example (or any material the mechanical properties of which vary with time), is placed between these two transducers. Preferably, these transducers are compressional ones (also known as immersion transducers) instead of contact transducers. Ultrasonic non-contact transducers are preferred because they do not suffer from shear coupling effects, occurring when using contact transducers. Actually, the shear coupling between the contact transducers and the sample introduces non-controllable variations in the signal amplitude and these variations can significantly disturb mathematical models used to estimate such measurements. The coupling for non-contact transducers is only dependent on the material parameters of the fluid medium 4 and the cement sample 3, those parameters being accounted for in the latter described model. Using non-contact transducers thus provide more accurate prediction of the propagation and detection of the acoustic waves through the sample.

The distance d between the transmitter and the receiver is chosen so as to accommodate a sample 3 of material (for example between 10 mm and 20 mm). The thickness h of this sample is such that it can be placed between the transducers at stand-off s with respect to each transducer, in order to be able to rotate the sample or the transducers as it will be described below. The sample of material 3 can be a set cement sample having a rectangular shape with known or measurable thickness along which acoustic signals can propagate. In this case, the method according to the invention will provide data on the evolution of the mechanical characteristics of this sample when, for example, submitted to temperature or pressure. In an other embodiment, cement slurry may also be accommodated inside containers of rectangular shape. In this case, the method according to the invention allows to follow the evolution of mechanical characteristics of a cement that is thickening, and consequently the thickening time and the mechanical properties of this cement after setting.

The cement sample is positioned preferably on a rotation stage such that its surfaces make an incidence angle theta (θ) with respect to the transducers sensitivity lines as shown in FIG. 1. For given incidence angles, θ, of the cement sample, ultrasonic data is acquired. FIG. 6 shows typical signals acquired from a sample of class H cement (well known in the API system), for h=15 mm, d=160.38 mm and a slurry density ρ=2000 kg/m³. For small values of θ including zero, the signals consist of contributions from compressional wave propagation in the sample. As θ increases, contributions from shear wave propagation arise. The compressional and shear events are identified on the signals in FIG. 6. The amplitude and transit time of these events will then be used in the model-based method described below to extract the compressional and shear velocities and attenuations.

FIG. 5a represents the structure of the apparatus according to the embodiment described in FIG. 1: a pair of piston transducers (preferably piezo-electric sensors) immersed in water is used in transmission mode to excite a layer of cement; data is acquired for normal incidence and oblique incidence θ as the cement layer is rotated with respect to its mid-plane about a rotation axis located at equal distance between the transmitter and the receiver. FIG. 5b represents the geometry of the configuration modelled theoretically: the transducers are aligned at an angle in the (x, z) plane. Their locations are θ-dependent.

Figure 2:
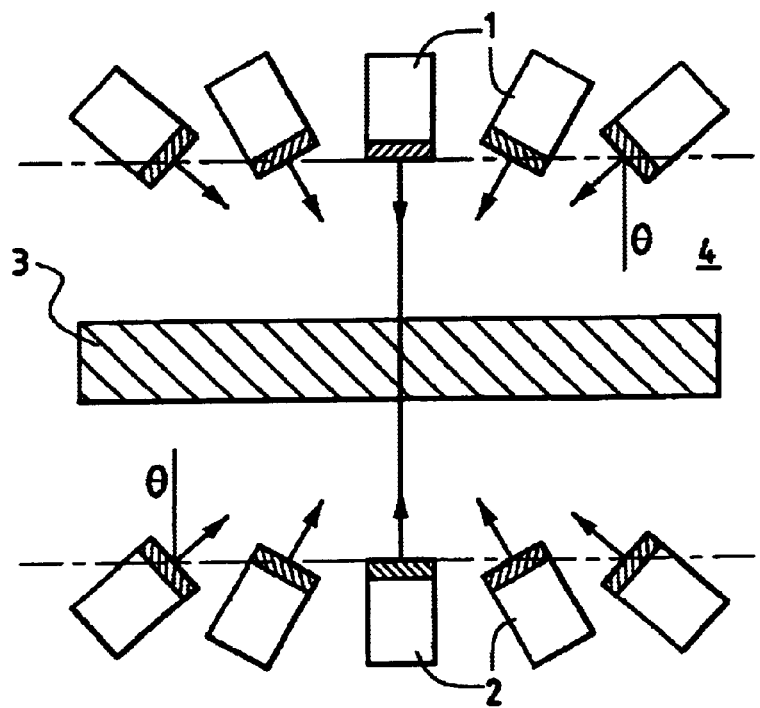
FIG. 2 is a second embodiment of the measurement apparatus of the invention.

A second preferred embodiment of the apparatus, shown in FIG. 2, consists of using multiple transmitters 1 and receivers 2 with a non-rotating sample 3. The transmitting and receiving elements are positioned and aligned at particular angles such that each transmitter-receiver pair has a beam incidence on the sample at a different angle. The number of pairs is chosen such that several incidence angles from zero to a maximum angle, θmax, are covered, i.e. most of the acoustic waves are detected by the receivers after they have passed through the sample. Depending on the sample tested, θmax may be near 40° for conventional cements and near 70° for cement with a large proportion of water. The large rotation angles are needed for this latter cements because their shear wave velocities are generally lower than the sound speed in the fluid.

Figure 3:
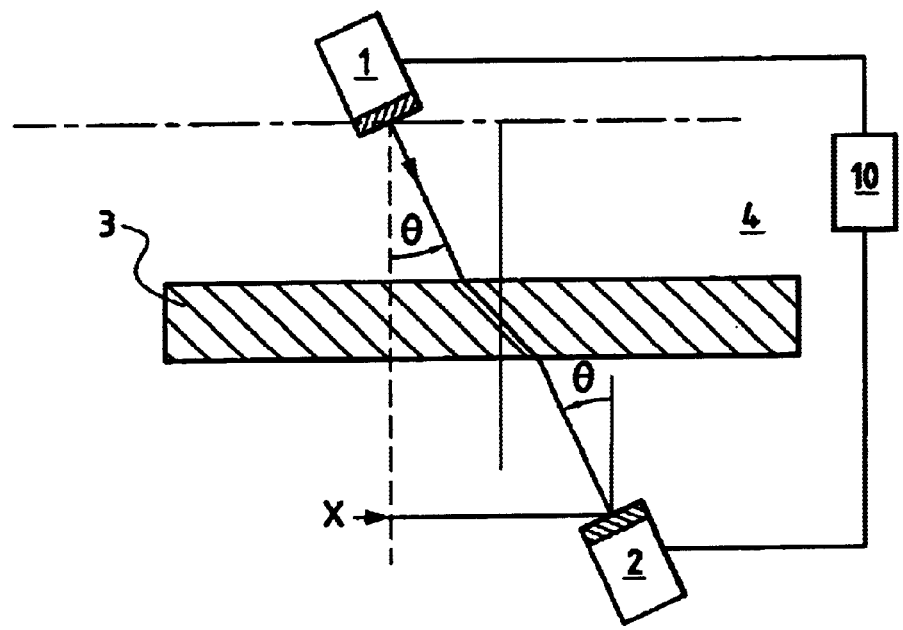
FIG. 3 is a third embodiment of the measurement apparatus of the invention.

A third preferred embodiment of the apparatus, shown in FIG. 3, consists of a single transmitter 1 and a single receiver 2 with the cement sample 3 in a fixed position. The transmitter and receiver alignment angles θ may be controlled via an external mechanism 10. The signals at θ=0 are used to determine the compressional wave velocity and attenuation. In addition, the receiver 2 may be translated along a line parallel to the sample surfaces, in order to capture the incident shear waves where their amplitudes are largest (see FIG. 3). The alignment angles of both transmitter and receiver are preferably chosen identical. The position of the receiver, denoted by $x_s$ is chosen according to a formula:

$$x_s = S_T \tan\theta + S_R \tan\theta + h \tan\theta_l$$

where l means either the shear (S) or compressional (P) waves, $S_T$ and $S_R$ are respectively the transmitter and receiver stand-offs from the sample nearest surface (measured when θ=0), and θ their alignment angles. This formula is such that the axis of maximum amplitude of the shear beam transmitted through the sample impinges on the receiver aperture close to its centre (as per FIG. 3) because it is the place where the efficiency of said receiver is optimal. In this formula $\theta_S$ is the axis of the transmitted shear beam:

$$\theta_S = \sin^{-1}\left[\frac{V_s}{V_f}\sin\theta\right] \quad [1]$$

Here $V_s$ and $V_f$ refer respectively to the velocity of the shear wave in the cement and sound speed in the medium in the absence of the sample. So for each incidence angle, the receiver is positioned at $x_S$ to capture the shear wave. Since the wave velocities in the cement are not known, one can use a guess value for the shear wave velocity and measure signals at various angles and receiver positions. The model-based method does not rely on accurate estimation of $x_S$ since it can account for arbitrary alignment and position of the receiver as described below.

Figure 4:
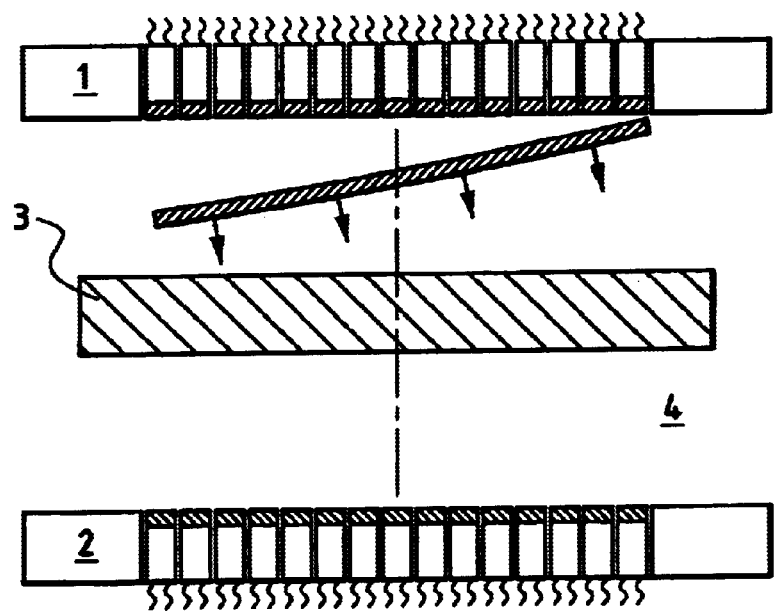
FIG. 4 is a fourth embodiment of the measurement apparatus of the invention

FIG. 4 represents an other embodiment of a measurement apparatus. In this embodiment, neither the transmitter and receiver nor the cement sample are rotated. Actually, the transmitter is constituted by an array of transducers that each emits acoustic waves that are spaced of a short period of time from one transducer to an other. Consequently, the wave front that is emitted towards the sample is globally inclined of an angle θ. This apparatus also has electronic means that allow to change the period of time spacing each wave, in order to modify the incidence angle θ of the front wave. In an other embodiment, it is the receiver that is constituted by an array of transducers that each detects acoustics waves that are time spaced from one transducer to another.

The embodiments described above refer to part of the ultrasonic subsystems 1', 2'. Accompanying these subsystems are ultrasonic pulser (frequency about 500 kHz), signal conditioning circuitry including low and high pass electronic filters, amplifiers, as well as mechanical subsystems capable of rotation and/or linear translation of the sample and/or the transducers when required. Additionally, special transducer housings or windows may be necessary to shield them from the high temperature and pressure measurement environment. If such devices are used, the theoretical model described here above may be extended to account for transmission of the acoustic waves through them.

After being detected by the receiver, the signals are compared to calculated signals provided by the calculating method. At the end of the iteration process, the method will extract the velocities and attenuations of the compressional and shear waves from ultrasonic signals acquired in a cement sample and finally provide the mechanical characteristics of said sample. The velocities are denoted by Vp and Vs and the attenuations by αp and αs. The calculating method is based on the use of a theoretical model that simulates the measurement technique implemented in the apparatus in order to provide signals corresponding to the measured signals and to compare these two sets of signals.

The inputs to the model consist of several parameters that describe the components of this measurement apparatus such as transducers, cement sample, medium fluid that separates transducers from the sample, as well as the system electronics. Each of these parameters is estimated. The velocities and the attenuation properties of the sample of tested material also constitute inputs parameters. These are estimated and initialised in the calculating method. This theoretical model is implemented in a computer 20 code using known programming languages. Additionally, an interface is developed, said interface permitting to drive the calculating code automatically and with minimal operator intervention.

For each set of measured signals, the computer code generates corresponding calculated signals. Certain attributes of the two sets of signals, such as transit times and amplitudes of particular events, are compared and differences noted. On the basis of these differences, the code specifies updates in the input parameters (one or few or all at a time) as detailed below. The new set of inputs is used to generate a second set of calculated signals and comparisons in the attributes are performed again, and so on. The iteration process stops when the differences in all the attributes are within a tolerance factor prescribed by the operator or when the number of iterations exceeds a prescribed maximum.

Optimal utilisation of the theoretical model and numerical code to calculate the cement parameters requires two calibration steps: 1) a characterisation of the radiation and reception properties of the transducers and 2) estimation of the transfer function of the electronics system which is not modelled, but is accounted for in the method according to the invention.

The transducer characterisation may be performed according to well known techniques in a laboratory setting using a water tank. In this measurement, the receiver scans the acoustic field radiated by the transmitter. The scan is performed on a plane preferably perpendicular to the transducers sensitivity lines. Then, the time-domain voltage signals are Fourier transformed to the frequency domain so as to obtain the transducers characteristics at each frequency component of the meaningful spectral range (which typically spans 50 kHz to 1000 kHz). The frequency-domain voltage serves as reference data in a mathematical model characterising the measurement of the transducer. By fitting the calculated data to the measured data at each frequency, the optimal width and distribution of the transducer apertures are obtained. These values constitute inputs to the calculating model for the cement properties.

Since environmental parameters such as temperature and pressure influence the responses of the transducers and their electronics, their transfer function is captured from signals gathered preferably with the cement measurement apparatus. For this purpose, the measurement of the propagation of the signal in the fluid medium without the cement sample is used. The normalisation step that permits extraction of the transfer function requires dividing the temporal spectrum of the measured signal by that of the calculated signal. An additional result of this calibration step is the estimation of the sound speed in the medium fluid. If the cement measurement is performed at various temperatures and pressures, then this calibration step (capturing of the transfer function) is required for each different set of temperature and pressure. Such a task may be accomplished without removing the sample from the apparatus but rather pushing the sample away from the line of sight of the transducers such that there is a clear fluid path for the signal.

The cement characterisation model still needs two additional inputs (besides the four parameters that have to be estimated (Vp, Vs, $\alpha$p, and $\alpha$s)). These are the cement density and its thickness (measured along the direction of signal propagation). Both of these parameters are measured independently using well known techniques such as buoyancy method for the density. If it is estimated that variations in temperature within the measurement apparatus leads to variations in the cement thickness that are larger than the estimated errors on its measurement, then this variations should be measured and taken into account in the calculation of the cement parameters.

After this calibration step is performed, the mathematical model according to the invention can be used. Once the computing system has provided—at the last iteration—the values for the velocities and attenuations for both shear and compressional waves signals from the receiver, these values have to be converted into known mechanical properties to determine the integrity of the cement. The mathematical relations between velocities and mechanical properties are as follows:

Let $\lambda$ and $\mu$ be respectively the well-known Lame constants ($\mu$ is also known as the shear modulus) of an elastic solid and E, v, and k, be Young's modulus, Poisson's ratio, and bulk modulus, respectively. These quantities are related to Vp (velocity of compressional waves), Vs (velocity of shear waves) and density $\rho$ of the tested material through the following:

$$\lambda = \rho \cdot (V_p^2 - 2 \cdot V_s^2) \quad \mu = \rho \cdot V_s^2;$$
$$E = \frac{\mu \cdot (3\lambda + 2\mu)}{\lambda + \mu} \quad \upsilon = \frac{\lambda}{2 \cdot (\lambda + \mu)};$$
$$k = \lambda + \frac{2}{3} \cdot \mu$$

[2]

In the data reported by the model, E, $\mu$, and k are expressed in units of pounds per square inch (psi). This is related to the SI unit Pa [kg/(ms2)] via the following relation:

$$E(psi) = \frac{E(Pa)}{6.894757 \cdot 10^3}$$

[3]

Now, the mathematical model used to implement inputs in the method according to the invention will be described in more detail:

In a preferred embodiment, the experiments take places inside a fluid medium (water for example) and the transducers are ultrasonically-pulsed acoustic piston ones propagating acoustic waves in transmission mode in a finite planar sample of cement (of thickness preferably between 10 mm and 20 mm).

Examples of a possible configuration and of its geometrical version where the cement layer is laterally infinite are shown in FIGS. 5(a) and (b). A Cartesian coordinate system (x, y, z) is used with the y axis pointing out of the plane of the paper. For this description of the model, the cement layer is assumed to be isotropic and homogeneous with propagating waves in the linear regime. However, these restrictions do not constitute a limitation of the calculating model as this latter can accommodate more advanced mathematical models for wave propagation in the cement layer. The transducer apertures have finite sizes in the (x, y, z). The transmitting (T) and receiving (R) transducers may be modelled via the known Complex-Transducer-Point (CTP) technique described for example in "A complex-transducer-point model for emitting and receiving ultrasonic transducers" from S. Zeroug, F. E. Stanke and R. Burridge in Wave motion Vol. 24, 21–40 1996. The CTP technique simulates piston transducers with Gaussian particle velocity distributions. The same technique can also be generalised to accommodate transducers with arbitrary distribution by weighted sums of these CTPs (ie, transducers modeled with the CTP technique). However, the formula given below [5] is general to account for arbitrary transducer aperture distributions and not restricted to CTPs.

The forward mathematical model calculates the receiver voltage due to the pressure wave transmitted through the cement. For this purpose, spectral plane-wave expansion and synthesis of all pertinent wave fields are used to solve for the radiation, propagation in the fluid and transmission through the cement, and reception processes. The spectral integral representing the receiver voltage is computed via a real-axis integration scheme. In the following, the main formula of the model are presented.

The time-domain voltage $e_T(t)$ generated by the transducer (R) in reception mode can be derived from its frequency-domain counterpart $E_R(\omega)$ as follows:

$$e_R(t) = \frac{1}{2\cdot\pi}\int E_R(\omega)\cdot e^{-i\omega t}d\omega \quad [4]$$

where $\omega$ is the angular frequency ($\omega = 2\pi f$, where f is the frequency).

In the calculating model, equation [4] is carried out via a Fast Fourier Transform (FFT) algorithm. $E(\omega)$ is given by:

$$E_R(\omega) = \frac{\omega\rho_f\gamma(\omega)}{4\pi^2}\int\int_{-\infty}^{\infty}\hat{v}_z^T(k)\cdot\hat{v}_z^R(-\xi)\Phi(k)\Gamma(k)\,dk \quad [5]$$

where $\hat{v}_z^T$ and $\hat{v}_z^R$ are the spectral plane-wave amplitudes of the normal components of the particle velocity wavefield across the transducer aperture, $\Gamma(k)$ is the spectral plane wave transmission coefficient that accounts for the acoustic wave interaction with the cement layer, and $\Phi$ is the "propagator" factor that translates the signal from the transmitter aperture to the sample entry surface and from the sample exit surface to the receiver aperture. In equation [5], $\gamma(\omega)$ is a frequency-dependent quantity introduced to account for the transfer function of the transmitter and receiver electronics; it is captured through a calibration procedure as described above. The propagator $\Phi$ is given by the relation:

$$\Phi(k) = -\frac{2}{\kappa_f}\cdot\exp\{i[k_x(\tilde{x}_R - \tilde{x}_T) + k_y(\tilde{y}_R - \tilde{y}_T) + \kappa_f(\tilde{z}_R - h - \tilde{z}_T)]\} \quad [6]$$

Various methods are available to express $$\hat{v}_z^{T,R}$$

for a rectangular or apodised velocity distribution of a piston transducer or a phased array with radiation or reception characteristics close to that of a piston transducer. In a preferred embodiment, radiating (T) and receiving (R) CTPs are used. In this case, $E_R(\omega)$ is conveniently expressed in the following equation [A detailed analysis can be found in the reference by Zeroug et al which is cited above]:

$$E_R(\omega) = \quad [8]$$
$$-\frac{\gamma(\omega)\omega\rho_f}{8\pi^2}\int_{-\infty}^{\infty}\int_{-\infty}^{\infty}\frac{\Gamma(k)}{\kappa_f}\times\exp\{i[k_x(\tilde{x}_R - \tilde{x}_T) + k_y(\tilde{y}_R - \tilde{y}_T) + \kappa_f(\tilde{z}_R - h - \tilde{z}_T)]\}dk_xdk_y$$

with:

$$k^2 = k_x^2 + k_y^2;\quad \kappa_f = \sqrt{k_f^2 - k^2};\quad k_f = \frac{\omega}{V_f};$$

where $\rho_f$ is the fluid density, Vf is the sound speed in the fluid, h is the cement layer thickness. The quantities ($\tilde{x}_{T,R}$, $\tilde{y}_{T,R}$, $\tilde{z}_{T,R}$) are the CTP coordinates of T and R. For fixed transducers located and aligned in the y=0 plane as shown in FIG. 5(b) with the sample rotated at angle $\theta$, these complex coordinates can be written as:

$$\tilde{x}_T = ib_T\sin\theta\quad \tilde{x}_R = d\sin\theta - ib_R\sin\theta;$$

$$\tilde{y}_T = y_T = 0\quad \tilde{y}_R = y_R = 0; \quad [9]$$

$$\tilde{z}_T = -\frac{d\cos\theta - h}{2} + ib_T\cos\theta\quad \tilde{z}_R = \frac{d\cos\theta + h}{2} - ib_R\cos\theta \quad [10]$$

with $b_{T,R} = \frac{k_f W_{T,R}^2}{2}$ [11]

Here, $W_{T,R}$ is the waist 1/e radius of the rotationally symmetric 3D Gaussian beams associated with T and R. From equation [11], $b_T$ and $b_R$ are identified as the Fresnel lengths of T and R. Since the real piston transducers have identical geometrical dimensions, we will assume that $b_T = b_R$.

The expression for $\Gamma(kx,ky)$ for an isotropic and homogeneous solid medium is given by:

$$\Gamma(k) = \frac{iY(A+S)}{(A+iY)(S-iY)} \quad [12]$$

where:

$A = A(k) = (k_s^2 - 2k^2)^2\tan(\kappa_p h/2) + 4k^2\kappa_s\kappa_p\tan(\kappa_s h/2)$ $S = S(k) = (k_s^2 - 2k^2)^2\cot(\kappa_p h/2) + 4k^2\kappa_s\kappa_p\cot(\kappa_s h/2)$ $Y = Y(k) = \rho k_s^4\kappa_p/\kappa_f$ [13]

and $\kappa_{p,s} = \sqrt{k_{p,s}^2 - k^2}$; $k_{p,s} = \omega/V_{p,s} + i\hat{\alpha}_{p,s}$ [14]

Here Vp, Vs, $\hat{\alpha}_p, \hat{\alpha}_s$ are the compressional and shear wave velocities and attenuations (expressed in Nepers/m), respectively, inside the cement, $\rho$ is the fluid-to-cement density ratio $\rho_f/\rho_c$, and S and A are known as the Lamb characteristic functions for the symmetric and anti-symmetric modes in the cement layer. The attenuations may further be expressed as linearly dependent on the frequency: $\hat{\alpha}_{p,s} = (\omega/2\pi)\cdot\alpha_{p,s}$; with a slope given by $\alpha_p$ and $\alpha_s$ (expressed in Nepers/m/Hz). This function is preferred because it easily fits the behaviour of conventional cements. However, other frequency dependencies, perhaps needed for certain special cements, can also be accommodated in the calculating method according to the invention.

The mathematical equations above are implemented numerically to provide the calculating model, which is used to generate signals corresponding to the measured signals.

In practical, the acoustic method according to the invention proceeds as the following:

Attributes are estimated from both the model-calculated and measured signals, said signals being voltages values as a function of time. In the preferred embodiment according to the invention, these attributes are:

transit times of the P (compressional) and S (shear) events which may be estimated from the first zero crossing.

amplitudes of the P and S events which may be defined as the peak-to-peak amplitude, the peak amplitude of the envelope of the analytical signal associated with the event, or the area underneath this envelope.

The attributes for the calculated and measured signals are compared and the differences used to update for the model calculations the values of the velocities and attenuations for the acoustic waves trough the sample of material. This iteration process stops when the differences reach a prescribed tolerance factor or a maximum iteration number. Those two possible stopping keys are previously chosen and implemented in the calculating model. In a preferred example, simple linear minimisers that have been found effective and robust for the various tests conducted are used. Other minimisation schemes such as based on least-square may be used.

For the velocities, the calculating iteration is the following: let, $$t_l^{ref}$$

be the transit time of the compressional waves event (P), in which case l≡P or of the shear waves event (S), in which case l≡S, in the measured signals. Let, $t_l$, be the corresponding transit time of the calculated signals with a certain value for the wave velocity, $V_l$. At the $i^{th}$ iteration (i≦N), $V_l$ is updated according to:

$$V_l^{j+1} = V_l^j + \delta_{V_l}; \text{ where } \delta_{V_l} = -\frac{t_l^{ref} - t_l}{t_l^{ref} - (d-h)/V_f} V_l^j \quad [15]$$

where l means either the shear (S) or compressional (P) waves, d is the inter-transducers distance, h is the cement sample thickness, and $V_f$ is the sound speed in the fluid, all assumed known from independent measurement or calibration steps. The iteration process stops when the relative difference between two successive iterates of $V_l$ is within a prescribed tolerance factor:

$$\left|\frac{\delta_{V_l}}{V_l}\right| < \varepsilon_{V_l} \quad [16]$$

The iteration process also stops if the number of iterations exceeds a prescribed maximum.

For the attenuations, the calculating system is the following: let $$A_l^{ref}$$

be the amplitude of the compressional or shear waves events in the measured signals (as per the definition given above. Let $A_l$ be the corresponding amplitude of the calculated signal with a certain value for the attenuation $\alpha_l$. At the $i^{th}$ iteration (i≦N) $\alpha_l$ is updated according to:

$$\alpha_l^{j+1} = \alpha_l^j + \delta_{\alpha_l}; \text{ where } \delta_{\alpha_l} = \frac{A_l^{ref} - A_l}{A_l^{ref}} \alpha_l^j \quad [17]$$

where l means either the shear (S) or compressional (P) waves.

The iteration over the attenuation stops when the relative difference between two successive iterates of $\alpha_l$ is within a prescribed tolerance factor:

$$\left|\frac{\delta_{\alpha_l}}{\alpha_l}\right| < \varepsilon_{\alpha_l} \quad [18]$$

The iteration process also stops if the number of iterations exceeds a prescribed maximum.

The mathematical model has been described for generating calculated signals corresponding to a single transmitter and a single receiver interacting with a cement sample immersed in a fluid medium under general conditions for the transducer and cement sample alignment angles and positions. In case of a measurement with an array of transducers (as previously described with FIG. 4), this model is adequate to calculate signals corresponding to the operation of a transmitting element to a receiving element or that of a transmitting array to a receiving array under the assumption that the beam of the transducer array has similar propagation properties to the beam radiated by a single transducer of width equal to several wavelength (the reference wavelength is measured in the fluid medium at the centre frequency of the transducer signal).

Different tests have been prosecuted at ambient temperature and atmospheric pressure on solid samples. Several cements have been tested:

| Description | Cement Density (kg/m³) | Vp (m/s) | Vs (m/s) | Attp (dB/cm/MHz) | Atts (dB/cm/MHz) | E (kpsi) | ν |
|---|---|---|---|---|---|---|---|
| Classical cement (API class G) | 2025 | 3736 | 2040 | 1.24 | 5.16 | 3109 | 0.29 |
| Flexible cement with XE901 | 1646 | 2921 | 1558 | 2.99 | 6.73 | 1509 | 0.3 |
| Flexible cement with XE900 | 1633 | 2518 | 1293 | 4.68 | 13.33 | 1046 | 0.32 |
| Foam cement (30% air) | 1388 | 2248 | 1287 | 12.93 | 12.68 | 838 | 0.26 |
| Foam cement (20% air) | 1420 | 2193 | 1179 | 8.1 | 11.98 | 743 | 0.3 |
| Lightweight cement 1 | 1819 | 3158 | 1797 | 0.37 | 7.69 | 2147 | 0.26 |
| Lightweight cement 2 | 1595 | 3064 | 1694 | 1.4 | 7.77 | 1700 | 0.28 |
| Lightweight cement 3 | 1470 | 2848 | 1496 | 0.89 | 4.45 | 1249 | 0.31 |
| Lightweight cement 4 | 1116 | 2786 | 1429 | 0.68 | 6.52 | 873 | 0.32 |

1 Classical cement (API class G): cement and water;
2 lightweight cements at various densities: formulations including micro-cement and hollow microspheres of alumino silicate and water;
3 Foam cements at various density: classical cement + foaming agent and air
4 Composite cements (flexible cement): cement and flexible particles (XE 900 and XE 911)

These show that the method according to the invention simply provide accurate mechanical property values of various material. Said mechanical properties can then be used as inputs in mathematical models to interpret data from known acoustic tools.

Different examples have also been handled with a set of measured signals acquired from a sample made of a conventional class H (API system) cement. FIGS. 7–12 show comparison, along different iteration steps, between calculated signals according to the method of the invention and measured signals.

FIG. 6 shows the entire set of signals acquired with the measurement apparatus. The lower signal in the figure, denoted by "Fluid path", corresponds to the absence of the cement sample. This signal is used for calibration purposes of the method (as previously explained). The rest of the signals are acquired in presence of the cement sample when rotated at various angles ranging from 0° to 35°. The signal at 0° may be used to extract the compressional wave velocity and attenuation. Signals at 20° and above feature shear wave events. One or more than one of these signals may be used to calculate the shear wave velocity and attenuation.

Figure 7:
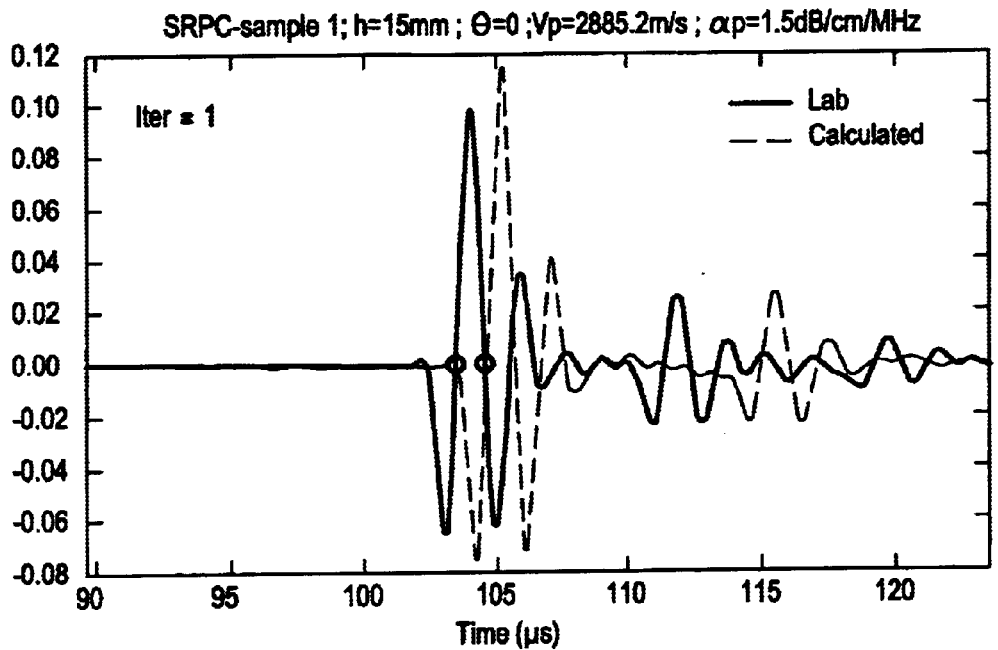
FIGS. 7 to 9 show measured and model-calculated signals for compressional waves velocities and attenuation estimation.
Figure 8:
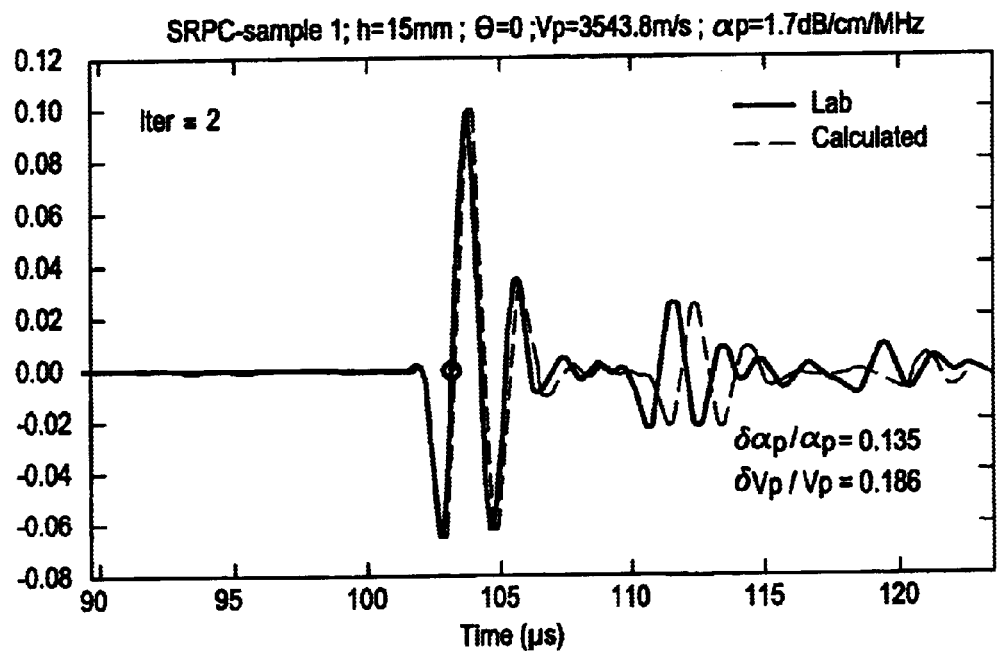
Figure 9:
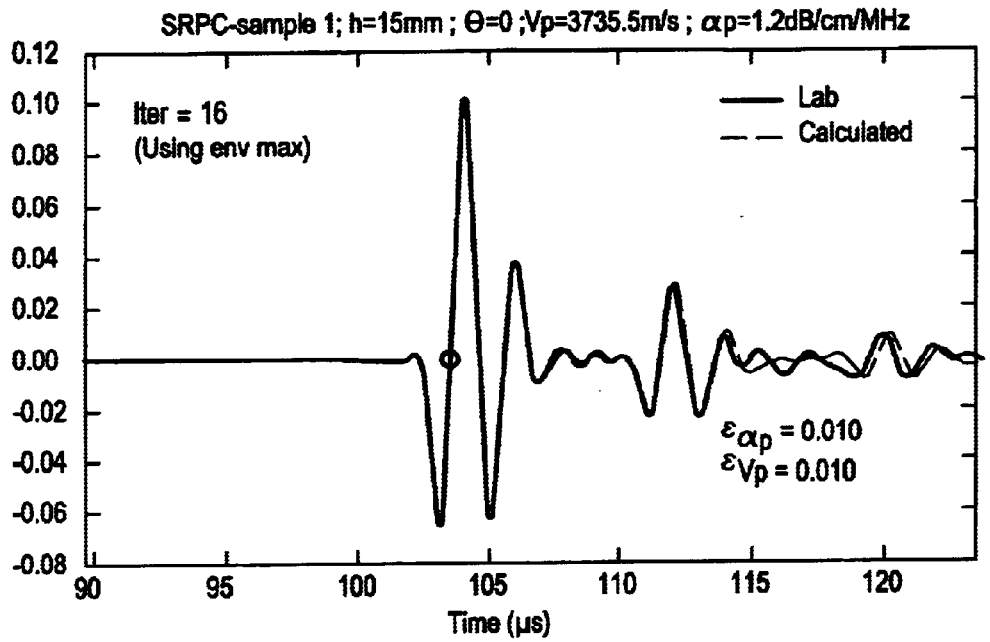

FIGS. 7, 8 and 9 show comparisons between the measured and model-calculated signals of compressional wave velocity and attenuation for a sample rotation of 0° generated at the first, second, and final iterations of the calculating algorithm. The tolerance criterion for both velocity and attenuation is selected at 1%. The optimal values for the final compressional wave properties of the cement are written in the title of the plot in FIG. 9.

Figure 10:
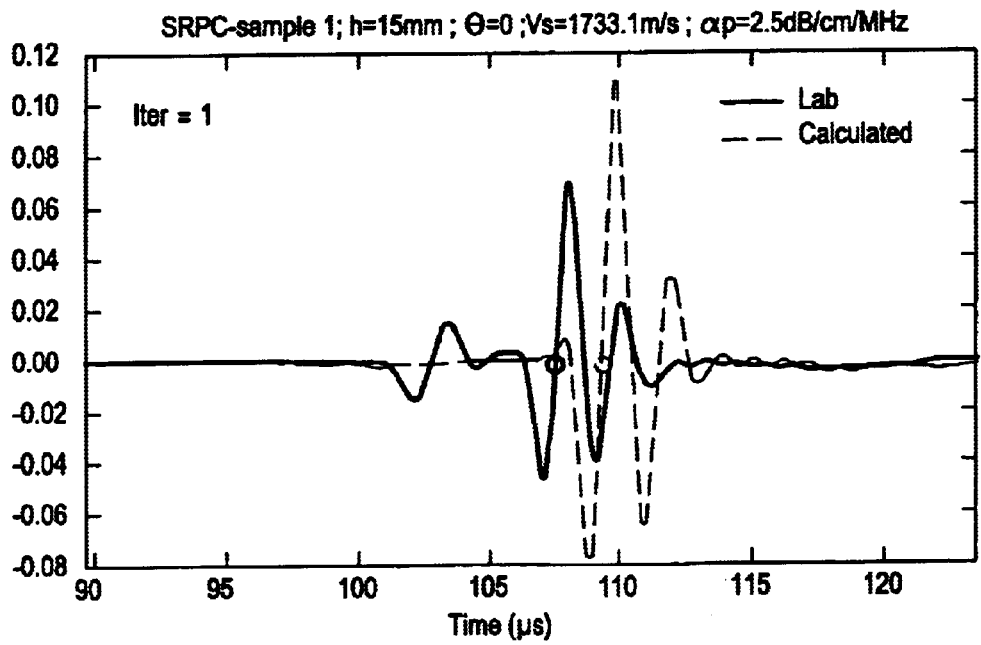
FIGS. 10 to 12 show measured and model-calculated data for shear waves velocities and attenuation signals.
Figure 11:
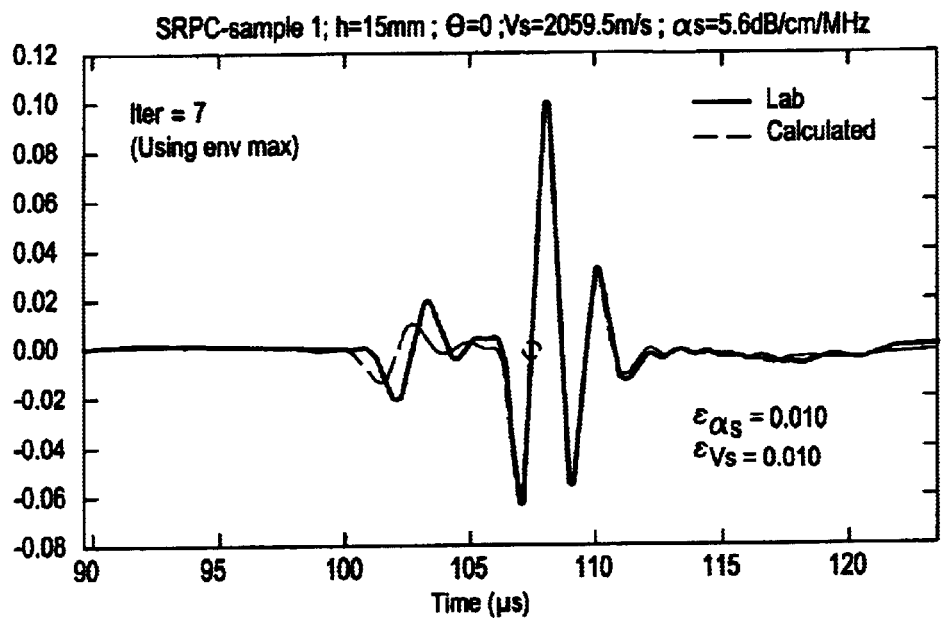
Figure 12:
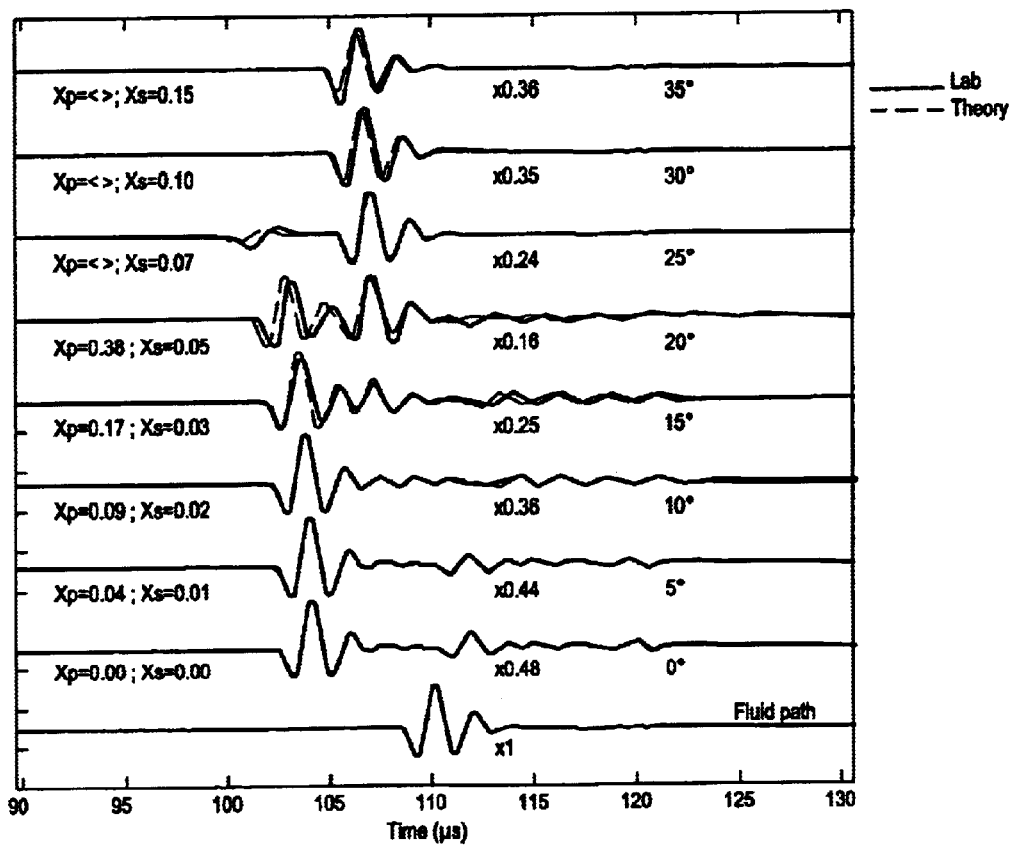

FIGS. 10, 11, 12 show comparisons between the measured and model-calculated signals of shear wave velocity and attenuation for a sample rotation of 25° generated at the first and final iterations of the calculating algorithm for the shear wave parameters. It can be noted that the discrepancy in the early compressional wave events is due to a limitation of the transducer characterisation model, which at this sample rotation affects only the compressional wave events and not the shear wave events. Also, the absence of the compressional wave event in the calculated signal at the first iteration is done purposely for shear event processing convenience. The tolerance criterion for both shear velocity and attenuation is selected at 1%. The optimal values for the final acoustic properties of the cement are written in the title of the plot in FIG. 12, the mechanical properties such as the Young's modulus, shear modules and Poisson's ratio are also calculated according to these final iterated acoustic characteristics.

Once the four mechanical parameters are calculated by the method for on the basis of two signals (a single rotational angle), a quality check can be performed using comparisons for signals at other sample rotation angles. FIG. 12 displays the results of such a quality control process.

The method according to the invention thus provides, from acoustic measurements through the cement sample, precious indications on the integrity of said cement, its thickening time in various temperature and pressure conditions. This method is consequently adapted to provide assessments on whether a particular cement is suitable for a particular cementing operation or how a particular cement will behave under particular well conditions.

What is claimed is:

1. A method for estimating the time varying mechanical properties of a cement comprising:
   (i) propagating acoustic waves through a sample (3) of the cement;
   (ii) measuring signals corresponding to the acoustic waves after propagated through the sample (3);
   (iii) comparing attributes from the measured signals with attributes from corresponding signals provided by a calculating model, the calculating model accounting for at least initially estimated acoustic properties of the cement;
   (iv) using the differences between the measured and calculated signals to update the initially estimated acoustic properties of the cement in the calculating model;
   (v) processing (N) iterations of comparison and updating until a predetermined calculating stop; and
   (vi) calculating the time varying mechanical properties of the cement from the final iterated acoustic properties; wherein the step of propagating acoustic waves through the sample comprises propagating acoustic waves at an incidence angle Θ to the surface of the sample of greater than zero so as to propagate shear waves through the sample.

2. The method as claimed in claim 1, comprising propagating both compressional and shear waves at the angle Θ.

3. The method as claimed in claim 1, wherein the predetermined calculating stop is the point at which the differences between measured and calculated signals are within a predetermined tolerance factor.

4. The method as claimed in claim 1, wherein the predetermined calculating stop is reached when the iteration number (N) reaches a predetermined maximum.

5. The method as claimed in claim 1, wherein the attributes of the measured and calculated signals are the transit times and amplitudes of the acoustic waves.

6. The method according to claim 5, wherein the acoustic properties of the cement comprise the velocity of the acoustic waves through the sample (3) of cement.

7. The method as claimed in claim 1, comprising propagating acoustic waves and measuring signals using ultrasonic compressional transmitter and receiver transducers.

8. The method as claimed in claim 7, further comprising the steps of immersing the transmitter (1) and the receiver (2) in a medium (4) and placing the sample (3) of cement between said transmitter and said receiver.

9. The method as claimed in claim 8, comprising updating the value of the velocity for the acoustic waves through the sample (3) of cement at the $i^{th}$ iteration (where $i \leq N$), according to:

$$V_l^{i+1} = V_l^i + \delta_{V_l}; \text{ where } \delta_{V_l} = -\frac{t_l^{ref} - t_l}{t_l^{ref} - (d-h)/V_f} V_l^i$$

where l is the shear (S) or compressional (P) wave, $t_l^{ref}$ is the transit time of the waves in the measured signals, $t_l$ is the corresponding transit time of the calculated signal with a certain value $V_l$ for the wave velocity, d is the distance between the propagating and the measuring means, h is the sample thickness, and $V_f$ is the sound speed in the medium.

10. The method as claimed in claim 9, comprising stopping iteration when the relative difference between two successive iterated values of the velocity for the acoustic waves through the sample (3) of cement is within a prescribed tolerance factor $\epsilon_{V_l}$:

$$\left| \frac{\delta_{V_l}}{V_l} \right| < \epsilon_{V_l}.$$

11. The method as claimed in claim 1, comprising calculating, as the time varying mechanical properties of the cement, the Young's modulus, the shear modulus and Poisson's ratio.

12. The method as claimed in claim 1, wherein the acoustic properties of the cement comprise attenuation of the acoustic waves through the sample of material.

13. The method as claimed in claim 12, comprising updating the value of the attenuation for the acoustic wave at the $i^{th}$ iteration ($i \leq N$), according to:

$$\alpha_l^{i+1} = \alpha_l^i + \delta_{\alpha_l}; \text{ where } \delta_{\alpha_l} = \frac{A_l^{ref} - A_l}{A_l^{ref}} \alpha_l^i$$

where l is the shear (S) or compressional (P) waves, $A_l^{ref}$ is the amplitude of the acoustic waves in the measured signals and $A_l$ is the corresponding amplitude of the calculated signal with a certain value for the attenuation $\alpha_l$.

14. The method as claimed in claim 13, comprising stopping iteration when the relative difference between two successive iterated values of the attenuation for the acoustic waves through the sample (3) of cement is within a prescribed tolerance factor $\epsilon_{v_l}$:

$$\left| \frac{\delta v_l}{V_l} \right| < \varepsilon_{V_l}.$$

15. The method as claimed in claim 1, comprising accounting for characteristics of the propagating and measuring means the calculating model.

16. The method as claimed in claim 15, wherein the characteristics of the propagating and measuring means comprise the radiation and the reception properties of the propagating and measuring means and the estimation of the transfer function of the electronic devices included in the means.

17. The method as claimed in claim 1, comprising accounting for environmental parameters in the calculating model.

18. An apparatus for propagating and measuring acoustic waves through a sample (3) of cement, the mechanical properties of which vary with time, the apparatus comprising:
(i) at least one transmitter (1) propagating acoustic waves towards at least one receiver (2), the receiver detecting the acoustic waves after they have passed through the sample; and means for calculating properties of the sample based on the detected acoustic waves; and
(ii) means for:
comparing attributes from the detected signals with attributes from corresponding signals provided by a calculating model, the calculating model accounting for at least initially estimated acoustic properties of the cement;
using the differences between the measured and calculated signals to update the initially estimated acoustic properties of the cement in the calculating model;
processing (N) iterations of comparison and updating until a predetermined calculating stop; and
calculating the time varying mechanical properties of the cement from the final iterated acoustic properties;
wherein the transmitter and receiver are arranged to propagate acoustic waves through the sample comprises propagating acoustic waves at an incidence angle Θ the surface of the sample of greater than zero so as to propagate shear waves through the sample; and means are provided for varying the incidence angle (θ) of the acoustic waves on the sample of the material.

19. The apparatus as claimed in claim 18, wherein the sample of material is rotationally mounted so as to allow its surface to make different incidence angles (θ) with respect to the transmitter and receiver sensitivity line.

20. The apparatus as claimed in claim 18, further comprising an external mechanism for controlling the alignment of the transmitter (1) and receiver (2).

21. The apparatus as claimed in claim 20, wherein the mechanism translates the receiver along a line parallel to the surface of the sample of cement.

22. The apparatus as claimed in claim 18, comprising multiple pairs of transmitters and receivers.

23. The apparatus as claimed in claim 22, wherein the transmitters and receivers are aligned from each part of the sample of cement such that each transmitter-receiver pair sensitivity line makes a different incidence angle (θ) with respect to the sample.

24. The apparatus as claimed in claim 22, wherein the number of pairs is such that several incidence angles (θ) from zero to a maximum angle are covered, the maximum angle being preferably greater than 30°.

25. The apparatus as claimed in claim 18, comprising an array of transducers that each respectively emits or detects acoustic waves that are time spaced from one transducer to another.

* * * * *